United States Patent
Beymer et al.

(10) Patent No.: US 8,594,398 B2
(45) Date of Patent: Nov. 26, 2013

(54) SYSTEMS AND METHODS FOR CARDIAC VIEW RECOGNITION AND DISEASE RECOGNITION

(75) Inventors: David James Beymer, San Jose, CA (US); Fei Wang, San Jose, CA (US); Tanveer Fathima Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 886 days.

(21) Appl. No.: 12/492,914

(22) Filed: Jun. 26, 2009

(65) Prior Publication Data

US 2010/0329521 A1 Dec. 30, 2010

(51) Int. Cl.
*G06K 9/00* (2006.01)

(52) U.S. Cl.
USPC ........... 382/128; 382/159; 382/203; 382/218; 382/224; 600/437

(58) Field of Classification Search
USPC ........... 382/128, 159, 203, 218, 224; 600/437
See application file for complete search history.

(56) References Cited

U.S. PATENT DOCUMENTS

| | | | |
|---|---|---|---|
| 6,346,124 B1 | 2/2002 | Geiser et al. | |
| 6,716,175 B2 | 4/2004 | Geiser et al. | |
| 7,668,354 B2 * | 2/2010 | O'Donnell et al. | 382/128 |
| 7,916,919 B2 * | 3/2011 | Zheng et al. | 382/131 |
| 2008/0260230 A1 * | 10/2008 | Gotardo et al. | 382/131 |
| 2010/0240996 A1 * | 9/2010 | Ionasec et al. | 600/443 |

OTHER PUBLICATIONS

Syeda-Mahmood et al., "Characterizing Spatio-temporal Patterns for Disease Discrimination in Cardiac Echo Videos", 2007, MICCAI 2007, Part I, LNCS 4791, pp. 261-269.*

Kumar et al., "Echocardiogram View Classification using Edge Filtered Scale-invariant Motion Features", Jun. 20, 2009, Computer Vision and Pattern Recognition, 2009. CVPR 2009. IEEE Conference on, 723-730.*

David Beymer and Tanver Syeda-Mahmood, Cardiac Disease Recognition in Echocardiograms Using Spatio-temporal Statistical Models, article, Aug. 23, 2008, published by IEEE Computer Society, 2001 L Street, NW. Suite 700, Washington, DC 20038-4910 USA.

David Beymer, Tanveer Syeda-Mahmood and Fei Wang, Exploiting Spatio-temporal Information for View Recognition in Cardiac Echo Videos, article, Jun. 27, 2008, published by IEEE Computer Society, 2001 L Street, NW, Suite 700, Washington, DC 20036-4910 USA.

(Continued)

*Primary Examiner* — David Zarka
*Assistant Examiner* — Katrina Fujita
(74) *Attorney, Agent, or Firm* — Cantor Colburn LLP

(57) ABSTRACT

A method for recognizing heart diseases in a cardiac echo video of a heart with an unknown disease using a spatio-temporal disease model derived from a training echo video, comprising the steps of: generating a plurality of training models for heart diseases, wherein the cardiac echo videos are each derived from a known viewpoint and the disease of the heart is known; analyzing the video of the heart with the unknown disease by fitting a model of shape and motion for each frame and combining the results across the frames; and, reporting the disease using a classification method for choosing among the diseases of interest.

13 Claims, 14 Drawing Sheets

(56) References Cited

OTHER PUBLICATIONS

Johan G. Bosch, Steven C. Mitchell, Boudewijn P.F. Leieveldt, Francisca Nijiland, Otto Kamp, Milan Sonka and Johan H.C. Reiber, Automatic Segmentation of Echocardiographic Sequences by Active Appearance Motion Models, article, Nov. 2002, IEEE Transactions on Medical Imaging, vol. 21, No. 11, It Is believed that the publisher is the Iowa Institute for Biomedical Imaging 3016B SC, Department of Electrical and Computer Engineering, The University of Iowa, Iowa City, IA 52242, USA.

Johan G. Bosch, Francisca Nijiland, Steven C. Mitchell, Boudewijn P.F. Leieveldt, Otto Kamp, Johan H.C. Reiber and Milan Sonka, Computer-aided Diagnosis via Model-based Shape Analysis: Automated Classification of Wall Motion Abnormalities in Echocardiograms, article, Academic Radiology, vol. 12, No. 3, Mar. 2005, It Is believed that the publisher is Leiden University Medical Center, Leiden, The Netherlands et al.

Dorin Comaniciu, Xiang Sean Zhou and Sriram Krishnan, Robust Real-Time Myocardial Border Tracking for Echocardiography: An Information Fusion Approach, article, Jul. 2004, vol. 23, No. 7, pp. 849-860, It Is believed that the publisher is the Iowa Institute for Biomedical Imaging 3016B SC, Department of Electrical and Computer Engineering, The University of Iowa, Iowa City, IA 52242, USA.

T.F. Cootes, C.J. Taylor, D.H. Taylor and J. Graham, Active Shape Models—Their Training and Application, article, 1995, pp. 38-59, vol. 61, No. 1, It is believed that this was published in Manchester, England, In Computer Vison and Image Understanding in 1995.

Shahram Ebadollahi, Shih-Fu Chang and Henry Wu, Automatic View Recognition in Echocardiogram Videos using Parta-Based Representation, article, Proceedings of the 2004 IEEE Computer Society Conference on Computer Vision and Pattern Recognition (CVPR'04), it is believed that this was published by the IEEE Computer Society, 2001 L Street N.W., Suite 700, Washington, DC 20038-4910, USA in 2004.

Schlomo V. Aschkenasy, Christian Jansen, Remo Osterwalder, Andre Linka, Michael Unser, Stephan Marsch, and Patrick Hunziker, Unsupervised Images Classification of Medical Ultrasound Data by Multiresolution Elastic Registration, article, Ultrasound in Med. & Biol., vol. 32, No. 7, pp. 1047-1054, 2006, it is believed that this was published by World Federation for Ultrasound in Medicine & Biology in the USA in 2008.

Paul Viola and Michael Jones, Rapid Object Detection using a Boosted Cascade of Simple Features, article, It is believed that this was published by the IEEE in the USA in 2001.

J. H. Park, S. K. Zhou, C. Simopoulos. J. Otsuki, and D. Comamiciu, Automatic Cardiac View Classication of Echocardiogram, article, at this time, it is believed that this article was published in the United States in 2007.

Todd R. Reed, Nancy E. Reed and Peter Fritzion, Heart sound analysis for symptom detection and computer-aided diagnosis, article, at this time, it is believed that this article was published by Elsevier B.V., Simulation Modelling Practice and Theory 12 (2004), pp. 129-146, in the United States.

Milan Sonka, Johan G. Bosch, Boudewijn P.F. Leieveldt, Steven C. Mitchelland Johan H.C. Reiber, Computer-aided diagnosis via model-based shape analysis: cardiac MR and echo, article, at this time it is believed that this was published International Congress Series 1256, in the United States in 2003, pp. 103-1018.

Rosaria Silipo and Carlo Marchesi, Artificial Neural Networks for Automatic ECG Analysis, article, IEEE Transactions on Signal Processing, vol. 46, No. 5, May 1998, at this time it is believed that this was published in the USA in May 1998.

Du-Yin Tsai, Comparison of Four Computer-Aided Diagnosis Schemes for Automated Discrimination of Myocardial Heart Disease, article, Proceedings of IEEE, International Conference on Signal Prooessing, 2000, it is behaved that this was published by the IEEE in the USA in 2000.

Du-Yih Tsai and Youngburn Lee, Fuzzy-Reason-Based Computer-Aided Diagnosis for Automated Discrimination of Myocardial Heart Disease from Ultrasonic Images, article, Electronics and Communications in Japan, Part 3, vol. 85, No. 11, 2002, at the present time, it is believed that this article was published by Wiley Periodicals, Inc., in 2002 and it also believed that the article may have been first published in Japanese and translated from Denshi Joho Tsushin Gakkai Ronbunshi, vol. J84-A, No. 12, Dec. 2001, pp.

S. Kevin Zhou, J.H. Park, B. Georgescu, C. Simopoulos, J. Otsuki, and D. Comamiciu, Image-based multiclass boosting and echocardiographic view classification, article, Proceedings of the 2008 IEEE Computer Society Conference on Computer Vision and Pattern Recognition (CVPR'06), it is believed that this article was published in the USA in 2006, and published by IEEE Computer Society, 2001 L Street, NW. Suite 700, Washington, DC 20036-4910 USA.

* cited by examiner

Procedure Train (training sequences)

seq' ← select portion of training sequences
annotate (seq') by hand
ASM ← ASM model building (seq')
fit ASM to all training sequences
{m} ← build motion vectors from ASM tracks
MotionModel ← dimensionality reduction ({m})
return (ASM, MotionModel)

FIG. 3B

Sequence I consists of m frames $I_1, \ldots, I_m$

Procedure Fit (Sequence I, ASM, MotionModel)

fit ASM to first frame $I_1$,
track with ASM model in
    frames $I_2, \ldots, I_m \rightarrow \Gamma_i, \mathbf{a}_i, \mathbf{b}_i$ $1 \leq i \leq m$ $\mathbf{m} \leftarrow$ build motion vector from ASM track
project onto MotionModel
    $\mathbf{c} \leftarrow M^T[\mathbf{m} - \overline{\mathbf{m}}]$ sequence fit $\leftarrow \dfrac{1}{m}\left[\sum_{i=1}^{m} \text{fit}(\mathbf{a}_i, \mathbf{b}_i, \Gamma_i)\right] +$
$\qquad\qquad \mathbf{c}^T \Sigma_{mot}^{-1} \mathbf{c} + 2 R_{mot}^2 / \lambda_{mot}^{r+1}$ return (sequence fit)

VIEW RECOGNITION

Input:
sequence I,
viewpoints v: 1, ... , V
training sequences

Model Building

View Recognition

View Recognition input: sequence I
    viewpoints v: 1 , ... , V
    training sequences Model Building
    for v from 1 to V
        ($ASM_v$, $MotionModel_v$) ← train (training data for view v)

View Recognition
    for v from 1 to V
        $fit_v$ ← fit (I, $ASM_v$, $MotionModel_v$)
    return $\mathrm{argmin}_v$ ($fit_v$)

FIG. 5B

Disease Recognition
    input:  sequence I
          viewpoints v: 1, ... , V
          diseases   d: 1, ... , D
          training sequences <u>model building</u>
    for d from 1 to D
        for v from 1 to V
            $(ASM_{d,v}, MotionModel_{d,v}) \leftarrow$
                Train (training data for disease d & view v)
        disease model (d) = $\bigcup_{v} (ASM_{d,v}, MotionModel_{d,v})$ <u>disease recognition</u>
    for d from 1 to D
        for v from 1 to V
            fit (d,v) $\leftarrow$ fit (I, $ASM_{d,v}, MotionModel_{d,v}$)
        fit (d) = $\operatorname*{ave}_{v}$ (fit(d,v))
    return $\operatorname*{argmin}_{d}$ fit (d)

FIG. 6C

SYSTEMS AND METHODS FOR CARDIAC VIEW RECOGNITION AND DISEASE RECOGNITION

FIELD OF THE INVENTION

Embodiments of the disclosure relate generally to the field of cardiac disease recognition. For example, embodiments of the disclosure relate to systems and methods for exploiting spatio-temporal information for view recognition and disease recognition in cardiac echo videos.

BACKGROUND

Echocardiography is used to diagnose cardiac disease related to heart motion. Among types of cardiac diseases diagnosed by employing echocardiography are disease involving regional motion, septal wall motion, and valvular motion abnormalities. Echocardiography provides images of cardiac structures and the movements of these structures, providing detailed anatomical and functional information about the functioning and health of the heart. These echocardiographs are taken from several standard viewpoints, such as apical 4-chamber view, parastemal long-axis view, parastemal short axis, and apical 2-chamber view.

Doctors regularly employ echocardiography as an aid to diagnosing disease. However, discerning motion abnormalities is difficult. For example, detecting when the myocardium contracts significantly less than the rest of the tissue is difficult because, unlike the interpretation of static images like X-rays, it is difficult for the human eye to describe and quantify the nature of an abnormality in a moving tissue. Thus, tools that automate the disease discrimination process by capturing and quantifying the complex three-dimensional non-rigid spatio-temporal heart motion can aid in disease detection.

SUMMARY

A method for determining a transducer position and a transducer viewpoint using spatial and temporal information in a cardiac echo video, comprising the steps of: receiving a spatial and temporal model for a known transducer viewpoint from a sample learning data; analyzing a new single heart-cycle echo sequence for the known transducer viewpoint by fitting a spatial aspect of the spatial and temporal model to each frame in the annotated cardiac echo cycle video, creating a time-varying set of spatial features; fitting the tracked spatial features to the motion model of the cardiac echo cycle, wherein the motion model is derived from the annotated cardiac echo cycle video; evaluating the spatial and temporal model fit using a combined fit of the motion model; receiving an appearance of a plurality of the heart-cycle variations using the plurality of heart-cycle variations for isolated features using the spatial and temporal models from the sample learning set; and, determining a matching model using a matching algorithm for recognizing the cardiac echo view from the appearance of the plurality of heart cycle variations.

A method for recognizing heart diseases in a cardiac echo video of a heart with an unknown disease using a spatio-temporal disease model derived from a training echo video, comprising the steps of: generating a plurality of training models for heart diseases, wherein the cardiac echo videos are each derived from a known viewpoint and the disease of the heart is known; analyzing the video of the heart with the unknown disease by fitting a model of shape and motion for each frame and combining the results across the frames; and, reporting the disease using a classification method for choosing among the diseases of interest.

These illustrative embodiments are mentioned not to limit or define the invention, but to provide examples to aid understanding thereof. Illustrative embodiments are discussed in the Detailed Description, and further description of the disclosure is provided there. Advantages offered by various embodiments of this disclosure may be further understood by examining this specification.

BRIEF DESCRIPTION OF THE DRAWINGS

These and other features, aspects, and advantages of the present invention are better understood when the following Detailed Description is read with reference to the accompanying drawings, wherein:

FIG. 3B shows an algorithm for the method for training spatio-temporal models of the heart from training sequences seen in the block diagram shown in FIG. 3A.

FIG. 4B shows an algorithm that fits the spatio-temporal models to a new echo sequence, as seen in the block diagram shown in FIG. 4A.

FIG. 5B shows an algorithm for recognizing cardiac viewpoint shown in FIG. 5A.

FIG. 6C is the algorithm for cardiac disease recognition.

DETAILED DESCRIPTION OF PREFERRED EMBODIMENTS

Embodiments of the disclosure relate generally to the field of disease recognition in the heart. For example, embodiments of the disclosure relate to systems and methods for exploiting spatio-temporal information for view recognition and disease recognition in cardiac echo videos. The inventors of the present invention have published an article entitled "Exploiting Spatio-temporal Information for View Recognition in Cardiac Echo Videos," and published by the IEEE Computer Society, 2001 L Street, NW. Suite 700, Washington, D.C. 20036-4910 USA, on Jun. 27, 2008, which is incorporated by reference into this application as if set forth fully herein. Two of the inventors also published an article entitled "Cardiac Disease Recognition in Echocardiograms Using Spatio-temporal Statistical Models," published by IEEE Engineering in Medicine and Biology Society, 445 Hoes Lane, Piscataway, N.J. 08854-4141 USA, on Aug. 23, 2008, which is incorporated by reference into this application as if fully set forth herein.

Throughout the description, for the purposes of explanation, numerous specific details are set forth in order to provide a thorough understanding of the present disclosure. It will be apparent, however, to one skilled in the art that the present disclosure may be practiced without some of these specific details.

Figure 1:
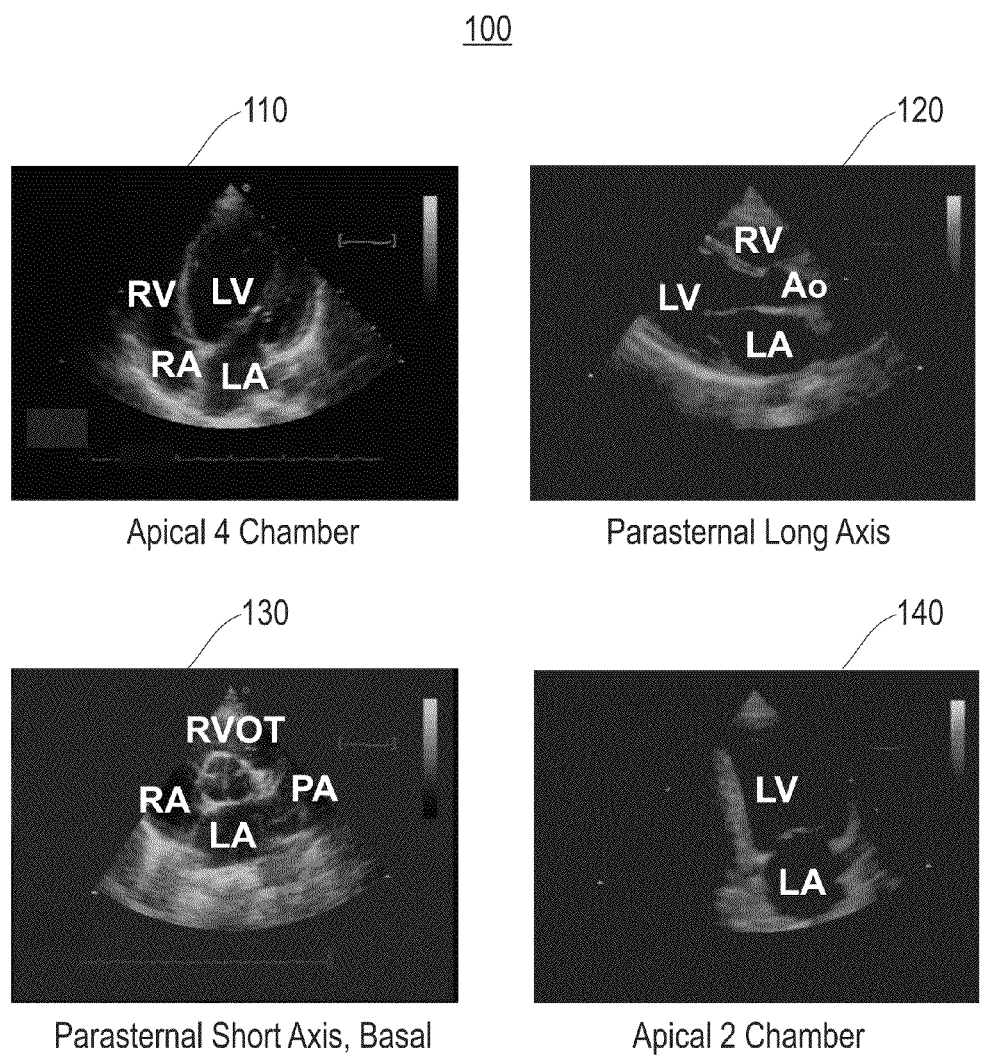
FIG. 1 illustrates different cardiac echo view points used in an echo cardiographic examination.

FIG. 1 is illustrates different cardiac echo view points used in an echo cardiographic examination. An echographic exam involves scanning a heart from four standard transducer positions, namely, parasternal, apical, subcostal and suprasternal. For each transducer position, the transducer is rotated and oriented to obtain multiple tomographic images of the heart along its long and short axes. Of the viewpoints generated by standard transducer positions, the most common are the apical 4-chamber 110, the parasternal long axis 120, the parasternal short axis 130 and the apical 2-chamber 140.

Tomographic imaging from the four standard transducer positions shows different combinations of anatomical regions of the heart, as illustrated in FIG. 1. Because different regions of the heart may be diseased without potentially affecting other regions, it is desirable to image the different regions of the heart. For example, Apical 4-chamber view 110 illustrates the left ventricle, left atrium, right ventricle, right atrium, septal wall, the mitral and tricuspid valves and can also be used to study left ventricle hypertrophy.

Figure 2A:
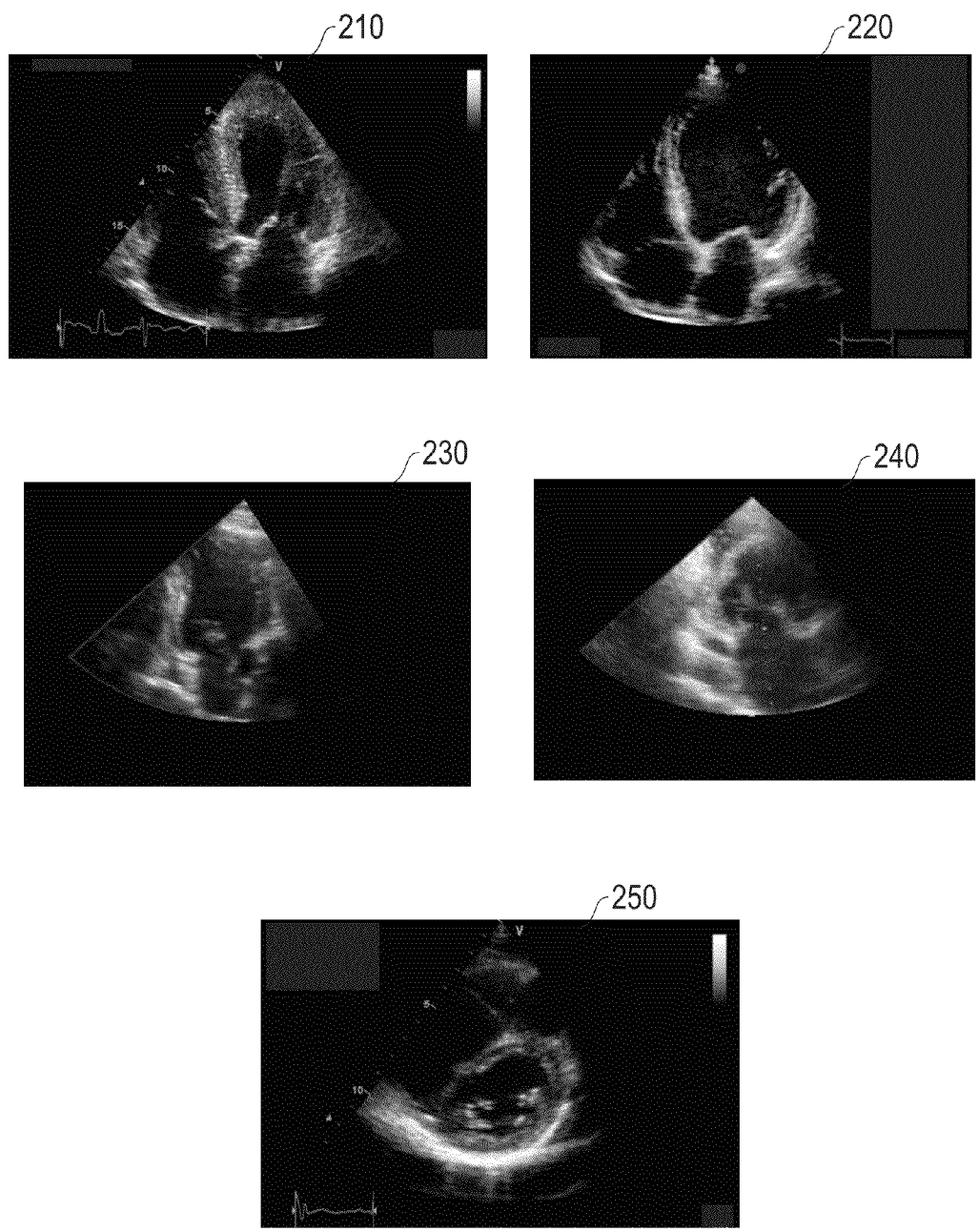
FIGS. 2A and 2B illustrate the variation in cardiac appearance within and between cardiac viewpoints and patients.
Figure 2B:
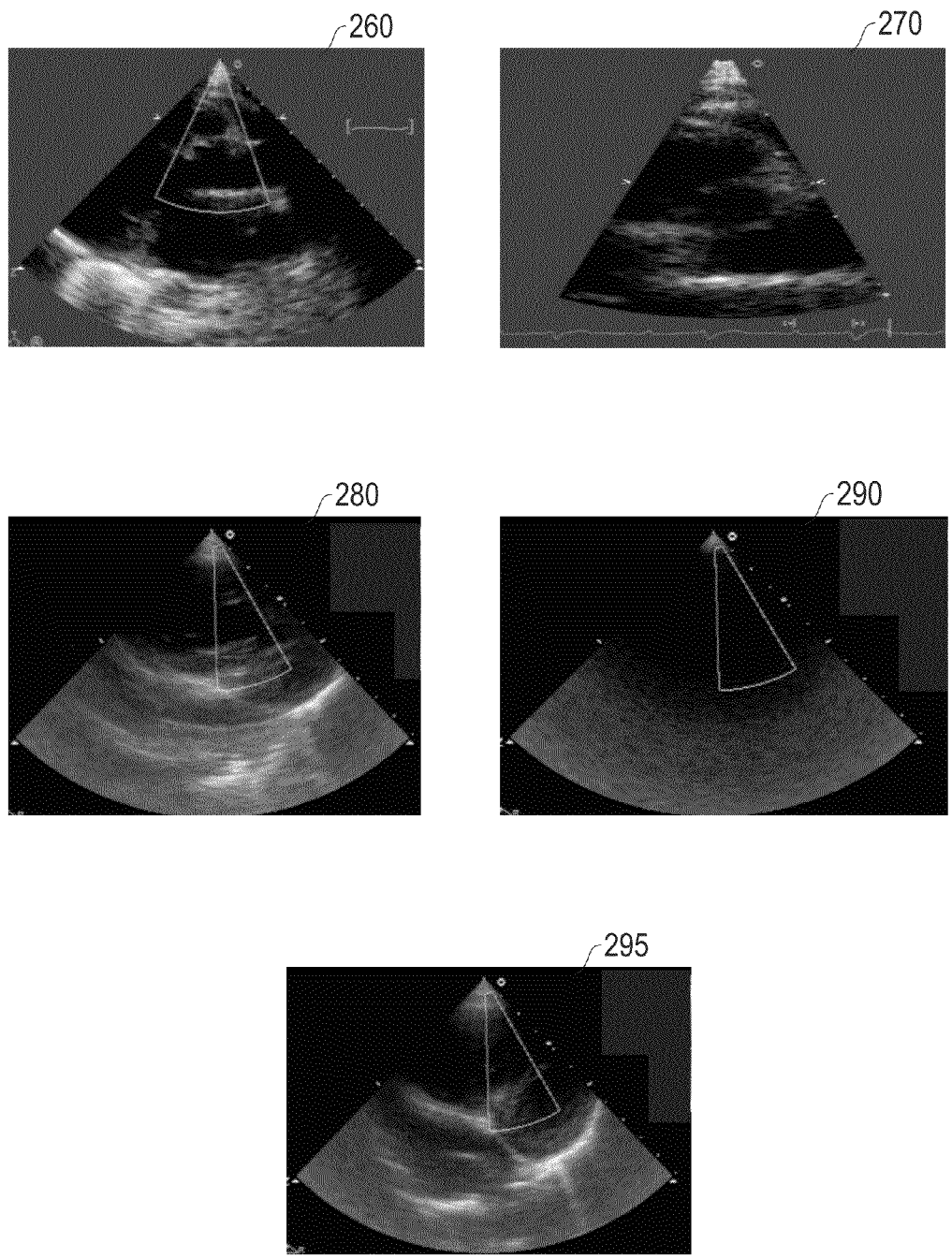

As seen in FIGS. 2A and 2B, there can be significant variation in the appearance of the heart for a given transducer position. This may be caused by anatomical differences between diseased and normal hearts as well as possibly due to a variety of other factors such as the variability between patients, instruments, operator experience or imaging modalities. Images 210 and 220 show a four-chambered view of two different hearts. Image 210 illustrates a patient with hypertrophy, while image 220 illustrates excessive enlargement of the left ventricle. Images 230, 240 and 250 show three different echocardiograph frames where 230 and 240 are 2-chamber viewpoints and the 250 is a short-axis viewpoint of the same heart. Thus, the echocardiograph of the same heart can generate very different images depending on the transducer position and image.

The effect of zoom and pan can also make the determination of viewpoint difficult. Images 260 and 270 illustrate this, where 270 is a zoomed in version of the region depicted in 260. The determination of viewpoint becomes even more challenging for real-time recordings, as it must distinguish standard viewpoints from transitional ones when the transducer is being moved before settling in a new position. Image 290 shows a transitional view that is from a continuous recording with before and after views shown in 280 and 295, respectively. Image 290 must be classified as a spurious view.

Figure 2C:
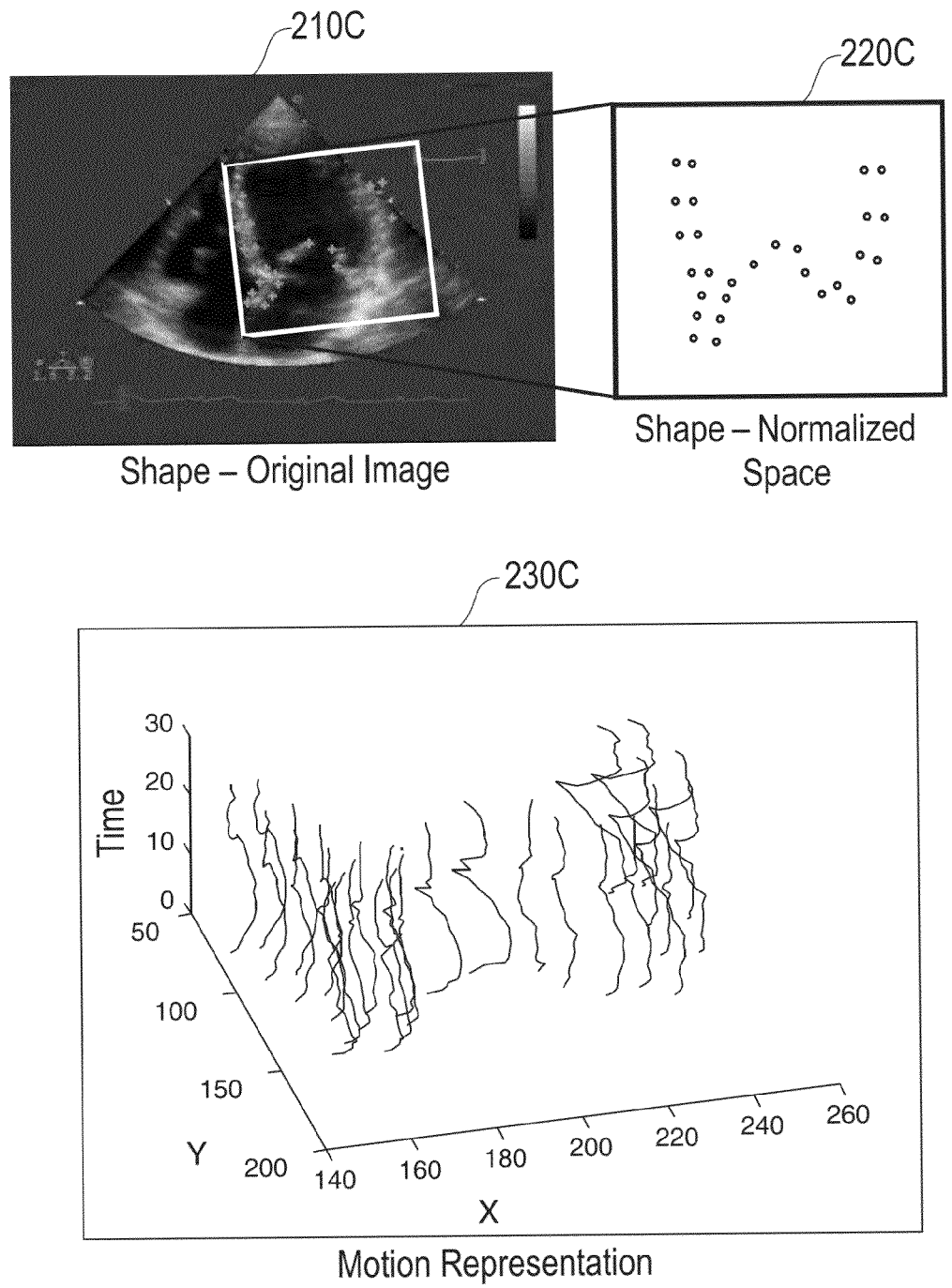
FIG. 2C shows a preferred embodiment of a visual appearance representation in a modeling approach of the present invention.

FIG. 2C shows a preferred embodiment of how visual appearance is represented by our modeling approach. Each image of a heart is represented by a shape vector s obtained by concatenating the (x, y) locations of n feature points $f_1, f_2 \ldots f_n$ as seen in 210C and in Equation (1). The shape vectors s are geometrically normalized by a similarity transform $\Gamma^{sim}$ that factors out variation in rotation, scale, and position. The final shape vectors are represented in a normalized space 220C. For instance, Procrustes analysis using two anchor points can be used for this normalization step. Thus, the full description of shape includes the vector s as well as a similarity transform $\Gamma^{sim}$ that positions the shape in the image through a rotation, scale, and a translation.

$$s = [x_1, y_1, K, x_n, y_n]^T \qquad \text{[Equation 1]}$$

Given an image with n features, the texture vector t concatenates the pixels from a set of patches centered on the feature points into a long vector, where patch size is matched to the pixel spacing between features. Just as the shape vectors are normalized for geometry, the texture vector $t_{raw}$ is similarly normalized for echo gain and offset by subtracting the mean and dividing by standard deviation as seen in Equation (2).

$$t = (t_{raw} - \bar{t}_{raw})/\sigma(t_{raw}) \qquad \text{[Equation 2]}$$

Since cardiac motion is a useful feature for cardiac analysis, we would also like to create a canonical representation of motion. Considering a cardiac cycle with m frames will produce m sets of feature points $\{s_1, s_2, \ldots, s_m\}$, where each s is a column vector of stacked shape (x,y) feature coordinates, as shown in 230C. To create a canonical representation, the motion of the cardiac cycle is vectorized by normalizing for image plane geometry and standardizing the time axis to a target length n.

Align the first frame $s_1$ to a canonical position using a similarity transform $\Gamma_1^{sim}$. To standardize the remaining frames i, $2 \leq i \leq m$, apply the same similarity transform to standardize the frames, as shown in Equation 3

$$s_i \leftarrow \Gamma_1^{sim}(s_i) \qquad \text{[Equation 3]}$$

To standardize the sequence length from input length m to a target length n, interpolate the $s_i$'s in time using piecewise linear interpolation. Next, to decouple shape from our motion representation, we factor out shape by subtracting out frame 1, creating our final motion vector m shown in Equation 4.

$$m = \begin{bmatrix} s_2 - s_1 \\ s_3 - s_1 \\ M \\ s_n - s_1 \end{bmatrix} \qquad \text{[Equation 4]}$$

In what follows, the shape, texture, and motion vectors are used to represent images both in model training and model fitting steps. In the model training step, a user trains the model representation by hand annotating the shape in all the training images. In contrast, the model fitting stage automatically fits a model of shape and texture to an input sequence to analyze.

Figure 3A:
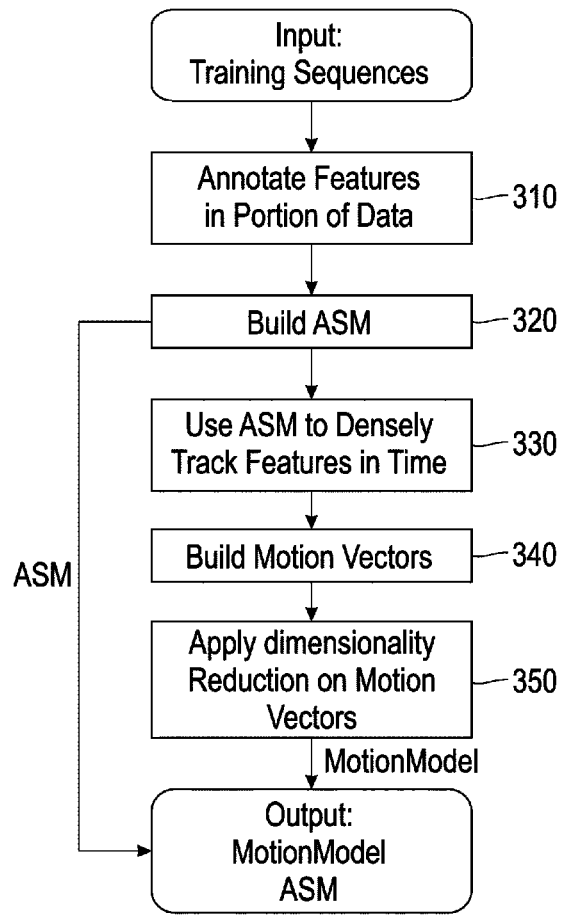
FIG. 3A is a block diagram representing a method for training spatio-temporal models of the heart from training sequences.

FIG. 3A is a block diagram illustrating an example method for training a spatiotemporal model of a heart 300. This may also be referred to as Training Stage Block Diagram 300. In one embodiment beginning at 310, a user first prepares a set of training data by annotating the (x, y) positions of feature points in the images, usually taken to sample along the contours of the heart walls and valves. In 320, the user builds an Active Shape Model (ASM), a spatial and textural model of heart appearance, for a known transducer viewpoint from the annotated training data. To construct the ASM model, the dimensional of the spatial and textural vector is reduced using PCA to find a small set of eignshapes and eigentextures. The shape s and the texture t can be linearly modeled to form the active shape model as seen in Equation (5).

$$s = Sa + \bar{s} \text{ and } t = Tb + \bar{t}, \text{ where} \qquad \text{[Equation 5]}$$

$$S = \begin{bmatrix} \vdots & \vdots & & \vdots \\ e_1^s & e_2^s & K & e_p^s \\ \vdots & \vdots & & \vdots \end{bmatrix} \text{ and}$$

$$T = \begin{bmatrix} \vdots & \vdots & & \vdots \\ e_1^t & e_2^t & K & e_q^t \\ \vdots & \vdots & & \vdots \end{bmatrix}$$

The p-dimensional vector a and the q-dimensional vector b are the low dimensional vector representations of shape and texture.

Proceeding to 330-350, a motion model is generated for a transducer viewpoint class by tracking the viewpoint's ASM within the training set of annotated echo sequences and modeling the resulting tracks with a linear generative motion model. In Block 330, the ASM model built in Block 320 is used to densely track the ASM feature points throughout the entire training data, which is necessary since the manual annotation step in Block 310 only requires a fraction of the training set to be hand-annotated. In Block 340 the ASM tracks are vectorized into motion vectors by normalizing for heart rate period and the positioning of the heart in the image. Block 350 applies a dimensionality reduction procedure to the training motion vectors, modeling them with a low-dimensional linear model, as shown in Equation 6.

$$m = Mc + \bar{m}, \text{ where} \qquad \text{[Equation 6]}$$

$$S = \begin{bmatrix} \vdots & \vdots & & \vdots \\ e_1^m & e_2^m & K & e_r^m \\ \vdots & \vdots & & \vdots \end{bmatrix}$$

The r-dimensional vector c is the low dimensional vector representations of motion, and the columns of matrix M are a set of r "eigenmotions" that form a low-dimensional basis for the cardiac motions seen in the training set.

The final output of the training procedure 300 is a viewpoint-specific ASM model and motion model.

FIG. 3B shows an algorithm for the method for training spatio-temporal models of the heart from training sequences seen in the block diagram shown in FIG. 3A.

Figure 4A:
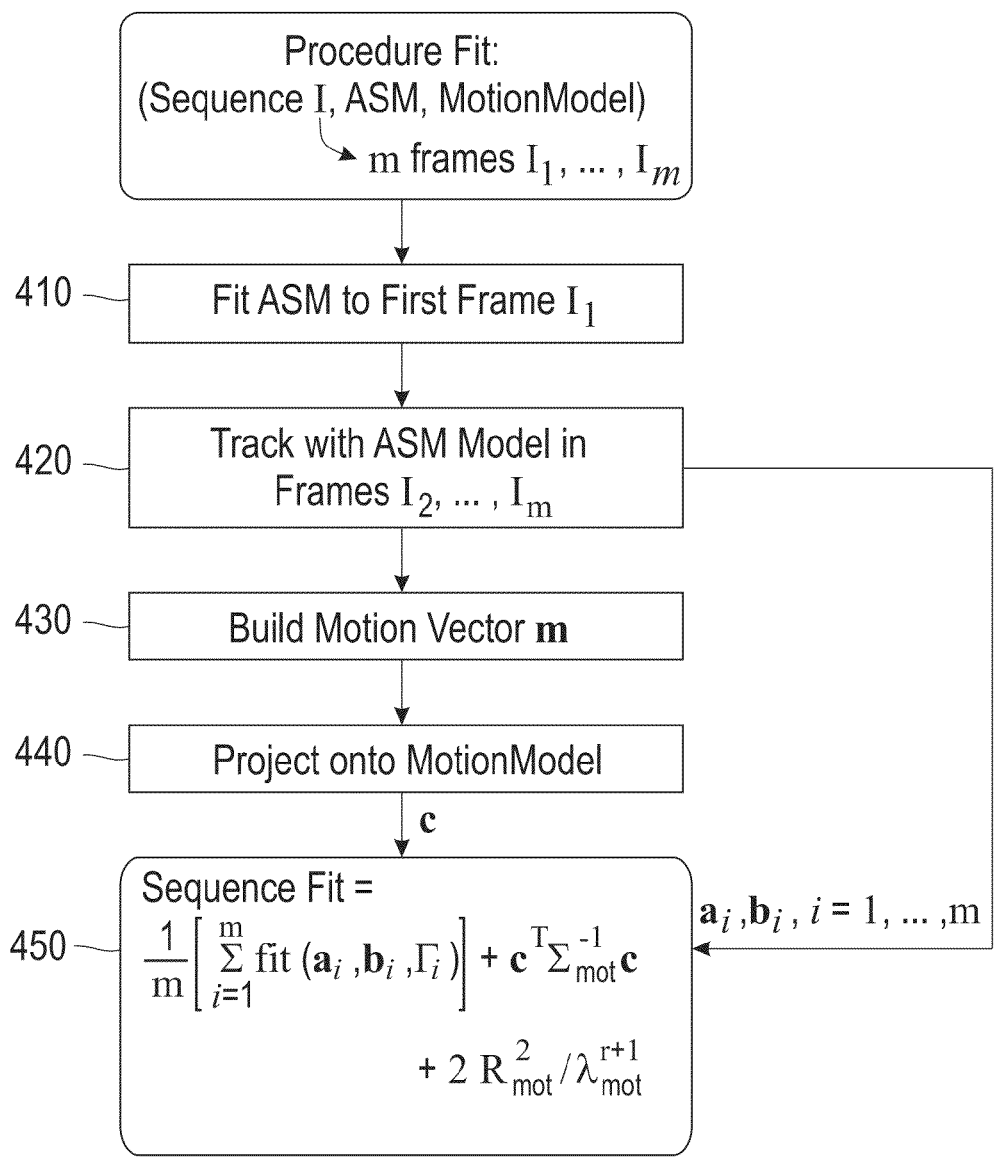
FIG. 4A is a block diagram of a fitting step that fits the spatiotemporal models to a new echo sequence to analyze.

FIG. 4A shows how the ASM and motion models from Block Diagram 300 can be fit to a new image sequence to extract heart shape and motion. This may be referred to as the Fitting Stage Block Diagram 400 In Block 410, the ASM model is fit to the first frame in the image sequence, image $I_1$. Since there is no prior information of the overall heart location in the image, this step is preceded by a segmentation step that locates the heart chambers. Given the initial ASM fit from $I_1$, Block 420 tracks the feature locations frame by frame through the remainder of the sequence using the ASM model.

Fitting an ASM to a new sequence involves finding a similarity transform $\Gamma^{sim}$ to position the model appropriately and recovering the shape and text vectors a and b. This is iteratively estimated by alternating between shape and texture update steps. To evaluate an ASM fit at a given position, error of fit is measured in shape and texture space using Mahalanobis distance and the normalized reconstruction error. For image I, this can be seen in Equation (7).

$$\text{fit}(a,b,\Gamma^{sim}) = a^T \Sigma_{shp}^{-1} a + b^T \Sigma_{tex}^{-1} b + 2R^2/\lambda_{tex}^{q+1} \qquad \text{[Equation 7]}$$

where $R = \|t - TT^T t\|$, $t = I(\Gamma^{sim}(x, y))$, $\lambda_{tex}^{q+1}$ is the $(q+1)^{th}$ texture eigenvalue, and $\Sigma_{shp}$ and $\Sigma_{tex}$ are diagonal matrices with PCA eigenvalues.

The overall motion of the ASM tracks from Block 420 is analyzed in Blocks 430-440. In Block 430, the ASM feature tracks are vectorized into a motion vector m, as in stage 340, normalizing for heart rate period and a global positioning transform. Proceeding to 440, the motion vector is projected into an eigen-motion feature space of a transducer viewpoint class, as shown in Equation (8).

$$c = M^T[m - \bar{m}], \qquad \text{[Equation 8]}$$

Proceeding to 450, the matching algorithm estimates a measure of a sequence fit for each cardiac view, wherein the sequence fit is an average appearance fit over the cardiac cycle plus a Mahalanobis distance and reconstruction error, as shown in Equation (9).

$$\text{sequence fit} = \frac{1}{m}\sum_{i=1}^{m} \text{fit}(a_i, b_i, \Gamma_i) + c^T \sum_{mot}^{-1} c + 2R_{mot}^2/\lambda_{mot}^{r+1}, \qquad \text{[Equation 9]}$$

where the function "fit" is defined in Equation (7), $R_{mot} = \|m - MM^T m\|$, $\lambda_{mot}^{r+1}$ is the $(r+1)^{th}$ texture eigenvalue, and $\Sigma_{mot}$ is a diagonal (r×r) matrix of eigenvalues corresponding to $e_1^m$, $e_2^m$, K, $e_r^m$. The Mahalanobis term is a weighted distance from the PCA projection of m to the mean motion $\bar{m}$ (but within the PCA model space). The reconstruction term measures the distance from m to the PCA projection of m, and it tells how well the model explains the data.

FIG. 4B shows an algorithm for fitting steps of the spatio-temporal models to a new echo sequence seen in the block diagram shown in FIG. 4A.

Figure 5A:
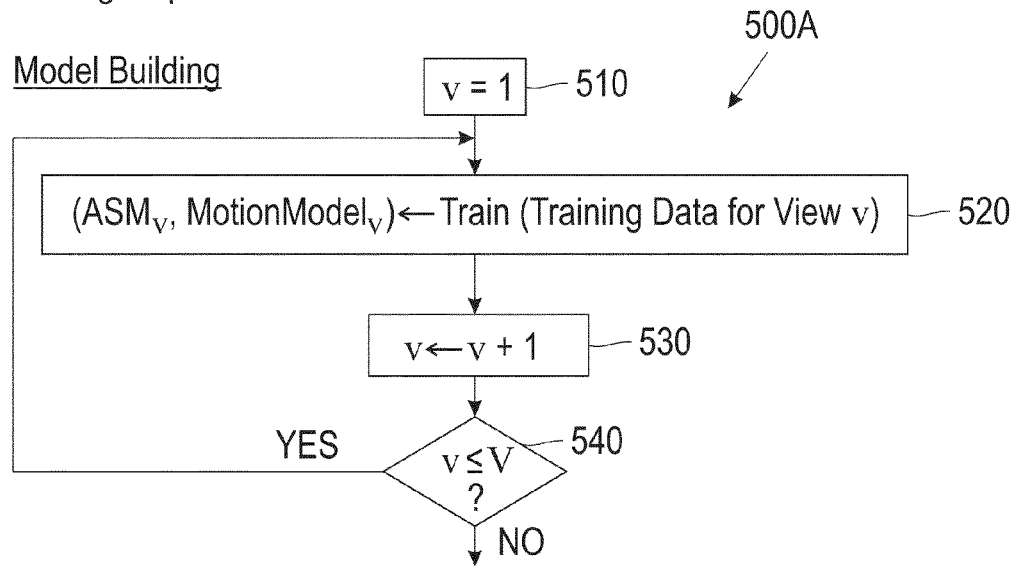
FIG. 5A is a block diagram of a method for recognizing cardiac viewpoint in echo sequences, divided into a model building stage and a runtime recognition stage.
Figure 5A:
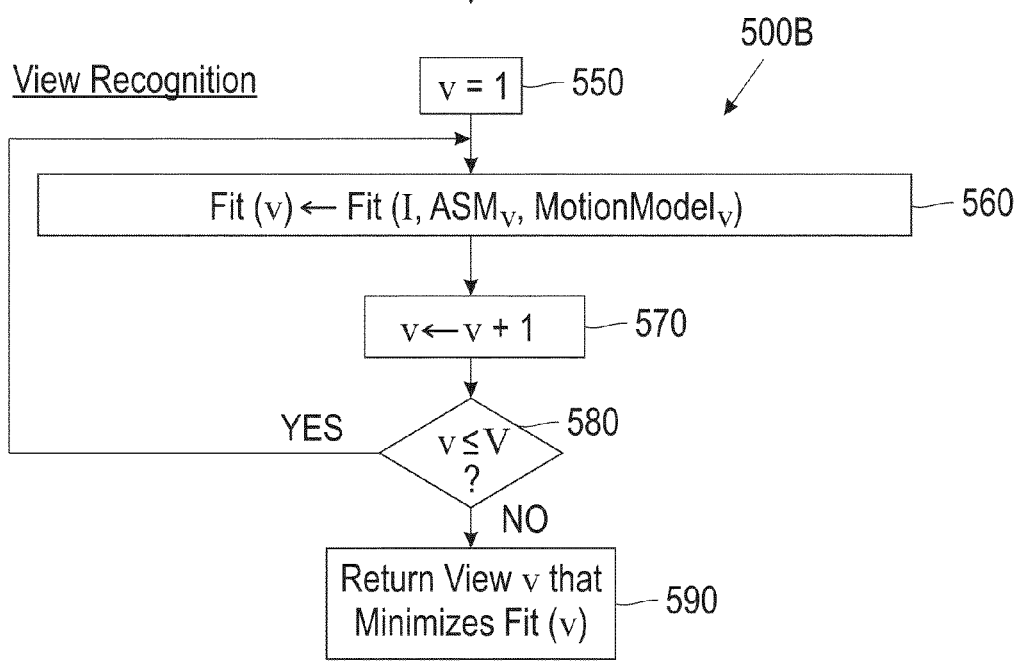

FIG. 5A is a block diagram 500 of a method for recognizing cardiac viewpoint in echo sequences, divided into a model building stage 500A and a runtime recognition stage 500B.

The Model Building Stage 500A iterates over all the viewpoints and builds a viewpoint-specific ASM and motion model for each viewpoint. The inputs for a 500A are a set of viewpoints v, 1≤v≤V, and a set of training sequences. In Block 510, the iteration variable v is initialized to 1 since this is the initial viewpoint. Proceeding to Block 520, ASM and motion models are built for viewpoint v from the training data specific for that viewpoint. This is implemented as a procedure call to the training block 300 in FIG. 3. After the ASM and motion models for view v=1 are completed, we move to the next viewpoint in Block 530 by increasing v by 1. In decision Block 540, the algorithm determines if the all available views v have been considered. If v is less than or equal to V, Blocks 520-530 are repeated. If v is greater than V, Model Building Stage 500A is completed.

View Recognition Stage 500B recognizes cardiac viewpoint v in input sequence I using the viewpoint-specific ASM and motion models generated by stage 500A. As in stage 500A, the view recognition algorithm iterates over the viewpoints v, and it returns the viewpoint with the best model fit. In Block 550, the iteration variable v is initialized to 1 since this is the initial viewpoint. Proceeding to Block 560, the viewpoint fit, fit(v) (see Equation 9), is computed by fitting the ASM and motion models for viewpoint v to input sequence I. Block 560 is implemented as a procedure call to the fitting block 400 in FIG. 4. After the model fitting is completed, we move to the next viewpoint in Block 570 by increasing v by 1. In decision Block 580, the algorithm determines if the all available views v have been considered. If v is less than or equal to V, Blocks 560-570 are repeated. If v is greater than V, we proceed to block 590, where the view v that minimizes fit(v) is returned as the recognized view.

FIG. 5B shows the algorithm for recognizing cardiac viewpoint shown in the block diagram of FIG. 5A.

Figure 6A:
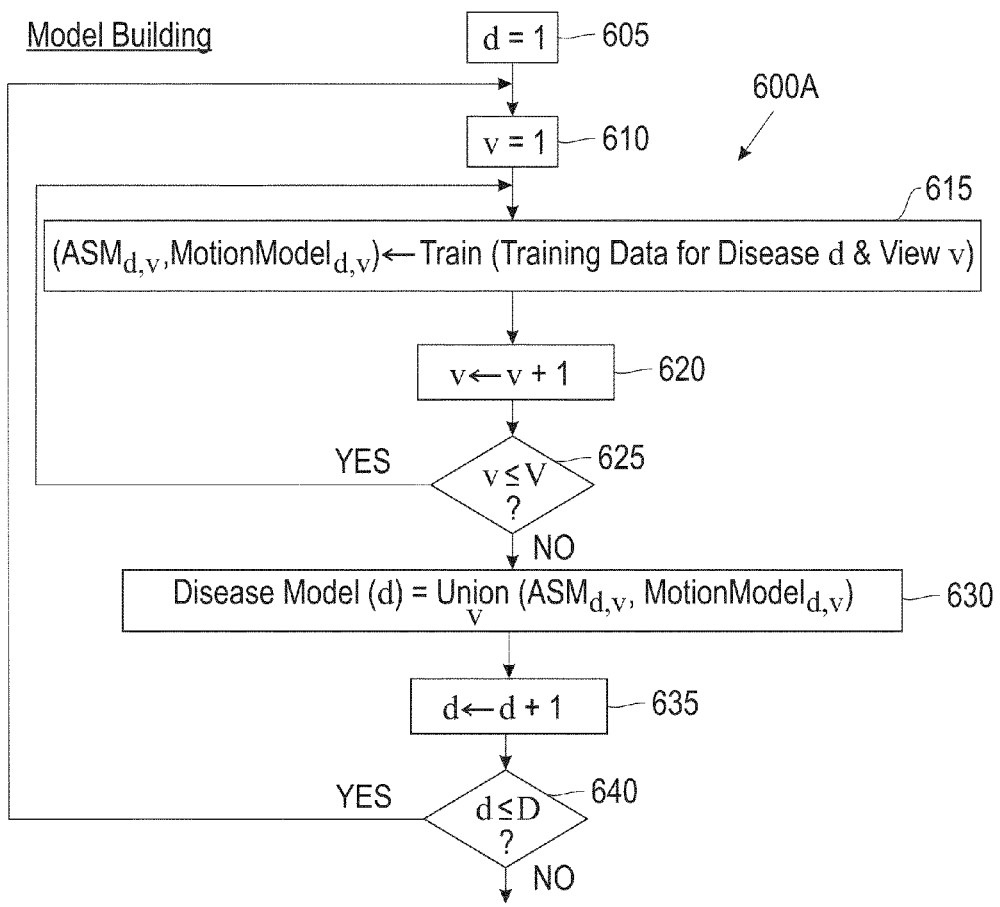
FIGS. 6A and 6B are block diagrams of a method for recognizing cardiac disease in echo sequences, divided into model building [FIG. 6A] and fitting [FIG. 6B] stages.
Figure 6B:
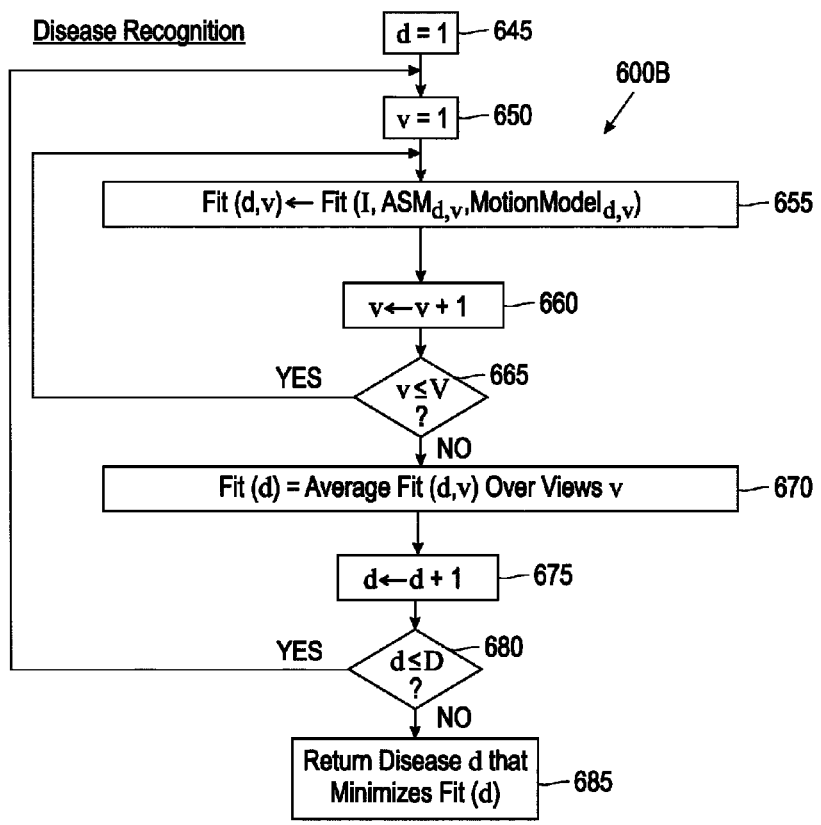

FIGS. 6A and 6B show a block diagram of Disease Recognition 600, which includes a model building portion 600A in FIG. 6A and a disease recognition portion 600B in FIG. 6B.

The model building portion 600A in FIG. 6A builds models for a set of diseases, where the disease models are, in turn, broken down into a collection of viewpoint-specific ASM and motion models. The inputs for 600A include a set of training sequences, viewpoints v, $1 \leq v \leq V$, and diseases d, $1 \leq d \leq D$. Block diagram 600A mostly consists of flow control over two nested loops, the outer loop over diseases d and an inner loop over viewpoints v. Block 605 begins with the first disease, d=1, and Block 610 begins with the first viewpoint, v=1. Block 615 creates an ASM and Motion Model for disease d and viewpoint v, using the training data for d and v. After model building and proceeding to Block 620, v is increased by 1. In decision Block 625, the algorithm determines if the all available views v have been modeled. If v is less than or equal to V, Blocks 615-620 are repeated to model an additional viewpoint.

When v is greater than V, the disease model for a particular disease, d, is the union of ASM(d,v) and MotionModel(d,v) over all the viewpoints v, as shown in Block 630. For example, a disease model for an enlarged heart would contain appearance-based ASM models that all generate enlarged chambers in all the viewpoints. It should be noted that the disease model also creates a "normal" model such that a healthy heart is part of the models included in this process. Thus, the process can recognize a healthy heart, rather than attempting to associate a heart disease with a healthy heart.

Block 635 shows the algorithm proceeding to the next disease and Block 640 shows a decision block that tests for additional diseases to model by comparing d with D. If d is less than or equal to D, the process repeats blocks 610-635 to model an additional disease. If d is greater than D, the model building stage 600A completes.

FIG. 6B is the Disease Recognition portion 600B of Block Diagram 600 and shows blocks 645, 650, 655, 660, 665, 670, 675, 680 and 685. The input to disease recognition is an input sequence I to classify, the disease models generated in 600A, viewpoints v, $1 \leq v \leq V$, and diseases d, $1 \leq d \leq D$. Similar to the model building portion 600A, disease recognition 600B consists of two nested loops, the outer loop over diseases d and an inner loop over viewpoints v. Block 645 begins with the first disease, d=1, and Block 650 begins with the first viewpoint, v=1. Block 655 fits the input sequence I to ASM and motion models for disease d and viewpoint v, which may be described by the algorithm in FIG. 4 and Equation 9, described above. Block 660 increments v by 1, moving to the next viewpoint. Decision Block 665 shows that if v is less than or equal to V, the process is returned to Block 655. If v is greater than V, the algorithm proceeds to Block 670, where the overall disease fit, fit(d), is taken as the average fit(d,v) over all views v. Block 675 moves to analyze the input I with the next disease, incrementing d by one. Decision Block 680 processes the next disease by returning to Block 650 if d is less than or equal to D. If d is greater than D, then we proceed to Block 685. Block 685 shows that the disease recognized by the algorithm is the disease that minimizes fit(d).

FIG. 6C shows the model building and disease recognition algorithms that correspond to Block Diagrams 600A and 600B.

Thus, at Block 685, the algorithm has recognized the heart disease most present in the patient in input sequence I. As discussed above, the null hypothesis is that the patient does not have a disease, wherein a normal class is also modeled. The diagnostic viewpoints of the normal class are taken as the union of viewpoints from all of the disease classes.

Exemplary Computer Architecture for Implementation of Systems and Methods

Figure 7:
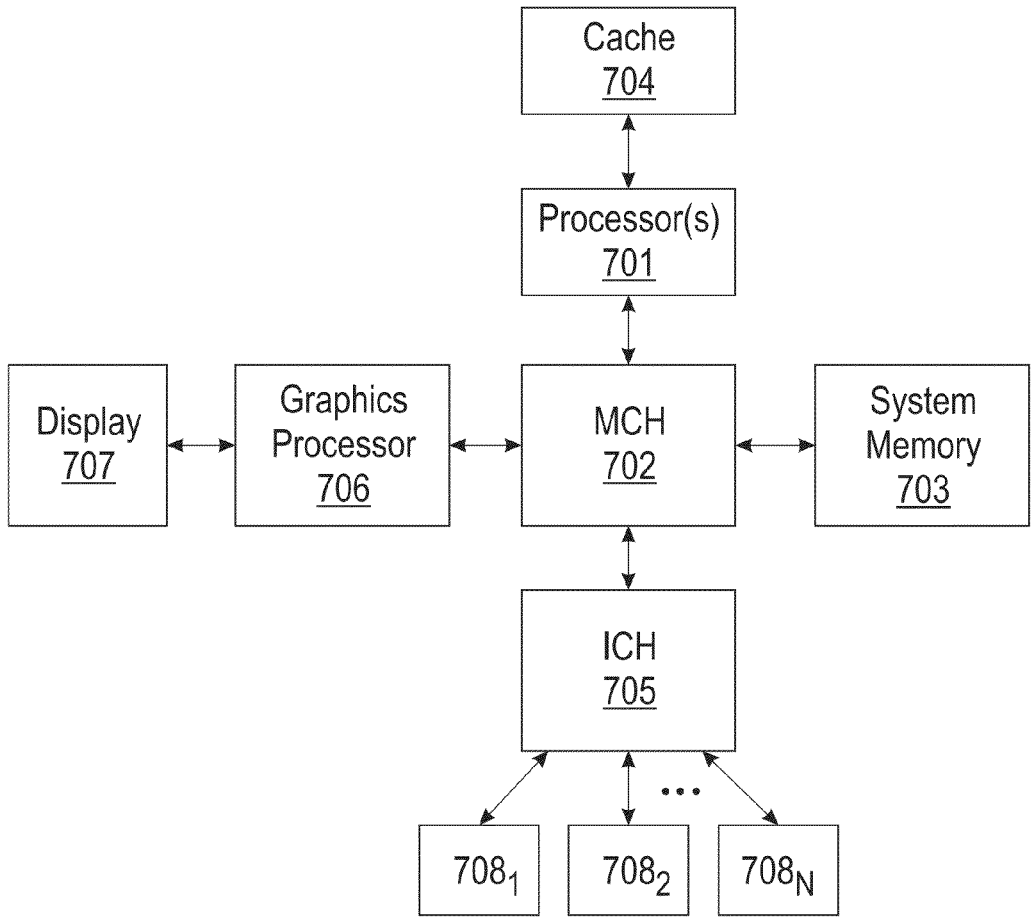
FIG. 7 is an example of computer architecture for implementing the embodiments as illustrated in FIGS. 3-6.

FIG. 7 illustrates an example computer architecture for implementing the methods and flows as described in FIGS. 3-6. The exemplary computing system of FIG. 7 includes: 1) one or more processors 701; 2) a memory control hub (MCH) 702; 3) a system memory 703 (of which different types exist such as DDR RAM, EDO RAM, etc,); 4) a cache 704; 5) an I/O control hub (ICH) 705; 6) a graphics processor 706; 7) a display/screen 707 (of which different types exist such as Cathode Ray Tube (CRT), Thin Film Transistor (TFT), Liquid Crystal Display (LCD), DPL, etc.); and/or 8) one or more I/O devices 708.

The one or more processors 701 execute instructions in order to perform whatever software routines the computing system implements. The instructions frequently involve some sort of operation performed upon data. Both data and instructions are stored in system memory 703 and cache 704. Cache 704 is typically designed to have shorter latency times than system memory 703. For example, cache 704 might be integrated onto the same silicon chip(s) as the processor(s) and/or constructed with faster SRAM cells whilst system memory 703 might be constructed with slower DRAM cells. By tending to store more frequently used instructions and data in the cache 704 as opposed to the system memory 703, the overall performance efficiency of the computing system improves.

System memory 703 is deliberately made available to other components within the computing system. For example, the data received from various interfaces to the computing system (e.g., keyboard and mouse, printer port, LAN port, modem port, etc.) or retrieved from an internal storage element of the computing system (e.g., hard disk drive) are often temporarily queued into system memory 703 prior to their being operated upon by the one or more processor(s) 701 in the implementation of a software program. Similarly, data that a software program determines should be sent from the computing system to an outside entity through one of the computing system interfaces, or stored into an internal storage element, is often temporarily queued in system memory 703 prior to its being transmitted or stored.

The ICH 705 is responsible for ensuring that such data is properly passed between the system memory 703 and its appropriate corresponding computing system interface (and internal storage device if the computing system is so designed). The MCH 702 is responsible for managing the various contending requests for system memory 703 access amongst the processor(s) 701, interfaces and internal storage elements that may proximately arise in time with respect to one another.

One or more I/O devices 708 are also implemented in a typical computing system. I/O devices generally are responsible for transferring data to and/or from the computing system (e.g., a networking adapter); or, for large-scale non-volatile storage within the computing system (e.g., hard disk drive). ICH 705 has bi-directional point-to-point links between itself and the observed I/O devices 708.

Referring back to FIGS. 3-6, portions of the different embodiments of the described methods and flows may be embodied in software, hardware, firmware, or any combination thereof. Any software may be software programs available to the public or special or general-purpose processors running proprietary or public software. The software may also be a specialized program written specifically for signature creation and organization and recompilation management.

For the exemplary methods illustrated in FIGS. 3-6, embodiments of the invention may include the various processes as set forth above. The processes may be embodied in machine-executable instructions that cause a general-purpose or special-purpose processor to perform certain steps. Alternatively, these processes may be performed by specific hardware components that contain hardwired logic for performing the processes, or by any combination of programmed computer components and custom hardware components.

Embodiments of the invention do not require all of the various processes presented, and it may be conceived by one skilled in the art as to how to practice the embodiments of the invention without specific processes presented or with extra processes not presented. For example, while it is described that a user may perform portions of the methods, those portions alternatively or in conjunction may be performed by an automated or computer process. In another embodiment, the models may be provided as previously generated.

GENERAL

The foregoing description of the embodiments of the invention has been presented only for the purpose of illustration and description and is not intended to be exhaustive or to limit the invention to the precise forms disclosed. Numerous modifications and adaptations are apparent to those skilled in the art without departing from the spirit and scope of the invention.

What is claimed is:

1. A method for recognizing heart disease in a cardiac echo video of a heart with an unknown disease using a spatio-temporal disease model derived from a training echo video, the method comprising:
    generating a plurality of training models for heart diseases, wherein the cardiac echo videos are each derived from a known viewpoint and the heart diseases of the heart are known;
    generating the plurality of training models for the heart diseases comprises building disease models for the heart diseases in which each of the disease models are for a plurality of viewpoints;
    analyzing the cardiac echo video of the heart with the unknown disease by fitting a model of shape and motion for each frame and combining the results across the frames, which comprises:
        applying an outer loop over the heart diseases and an inner loop for the plurality of viewpoints, where an input of sequences is for the cardiac echo video of the heart with the unknown disease;
        iteratively fitting each of the plurality of viewpoints for a first of the heart diseases during the inner loop until all of the plurality of viewpoints for the first of the heart diseases is finished;
        taking an overall disease fit for the first of the heart diseases over all of the plurality of viewpoints for the first of the heat diseases;
        continuing until a last of the heart diseases has been reached for the outer loop; and
        recognizing a heart disease of the heart diseases that minimizes the fitting after completing the outer loop; and
    reporting the heart disease using a classification method for choosing among the heart diseases of interest.

2. The method of claim 1, where the shape model is an active shape model.
3. The method of claim 1, where the motion model is a linear motion model.
4. The method of claim 1, where the motion of the entire video is analyzed by projecting onto the motion model.
5. The method of claim 1, where the fitting metric of the motion model is added to the average shape model fit across the frames.
6. The method of claim 1, where a fit for known diseases is calculated by averaging across each of the viewpoint dependent fits.
7. The method of claim 1, where the combining the results across the frames uses an average across the frames.
8. The method of claim 1, where the combining the results across the frames uses a median across the frames.
9. The method of claim 1, where the classification method is based on a neural network.
10. The method of claim 1, where the classification method is based on an support vector machine network.
11. The method of claim 1, where the classification method is based on a multilayer perceptron.
12. The method of claim 1, where the classification method is based on a radial basis function network.
13. A computer program product comprising a memory to store a computer readable program, wherein the computer readable program, when executed on a computer, causes the computer to perform for operations for recognizing disease, comprising:
    generating a plurality of training models for heart diseases, wherein the cardiac echo videos are each derived from a known viewpoint and the heart diseases of the heart are known;
    the plurality of training models for the heart diseases comprises building disease models for the heart diseases in which each of the disease models are for a plurality of viewpoints;
    analyzing the cardiac video of the heart with the unknown disease by fitting a model of shape and motion for each frame and combining the results across the frames, which comprises:
        applying an outer loop over the heart diseases and an inner loop for the plurality of viewpoints, where an input of sequences is for the cardiac echo video of the heart with the unknown disease;
        iteratively fitting each of the plurality of viewpoints for a first of the heart diseases during the inner loop until all of the plurality of viewpoints for the first of the heart diseases is finished;
        taking an overall disease fit for the first of the heart diseases over all of the plurality of viewpoints for the first of the heat diseases;
        continuing until a last of the heart diseases has been reached for the outer loop; and
        recognizing a heart disease of the heart diseases that minimizes the fitting after completing the outer loop; and
    reporting the heart disease using a classification method for choosing among the heart diseases of interest.

* * * * *